(12) United States Patent
Hall et al.

(10) Patent No.: US 6,511,177 B1
(45) Date of Patent: Jan. 28, 2003

(54) PROTECTIVE EYEWEAR WITH ADJUSTABLE STRAP

(75) Inventors: James Hall, Lincoln, RI (US); Keith Fecteau, Wilbraham, MA (US); Raoul Desy, Sturbridge, MA (US); John Salce, Auburn, MA (US)

(73) Assignee: Cabot Safety Intermediate Corporation, Southbridge, MA (US)

( * ) Notice: Subject to any disclaimer, the term of this patent is extended or adjusted under 35 U.S.C. 154(b) by 0 days.

(21) Appl. No.: 09/474,045

(22) Filed: Dec. 28, 1999

Related U.S. Application Data (60) Division of application No. 08/806,595, filed on Feb. 26, 1997, now Pat. No. 6,024,446, which is a continuation-in-part of application No. 08/641,901, filed on May 2, 1996, now abandoned, and a continuation-in-part of application No. 08/770,920, filed on Dec. 20, 1996, now Pat. No. 5,909,267.

(51) Int. Cl.⁷ .............................................. G02C 1/00
(52) U.S. Cl. ..................... 351/158; 351/119; 351/140
(58) Field of Search ............................ 351/44, 41, 111, 351/120, 121, 156–158, 140; 2/440, 441, 445, 448, 452, 453

(56) References Cited

U.S. PATENT DOCUMENTS

| | | | |
|---|---|---|---|
| 289,740 A | 12/1883 | Willson et al. | 351/154 |
| 836,599 A | 11/1906 | McKee et al. | 351/140 |
| 1,032,488 A | 7/1912 | Marcher | 351/121 |
| 1,119,811 A | 12/1914 | Day | 351/121 |
| 1,181,365 A | 5/1916 | Beaudry | 351/121 |
| 1,189,986 A | 7/1916 | Merry | 351/121 |
| 1,217,035 A | 2/1917 | McDowell | 351/121 |
| 1,250,703 A | 12/1917 | Hamilton et al. | 351/121 |
| 1,274,870 A | 8/1918 | Golding | 351/121 |
| 1,278,190 A | 9/1918 | Martin | 351/121 |
| 1,294,390 A | 2/1919 | Burke | 351/121 |
| 2,004,005 A | 6/1935 | McDanal | 351/140 |
| D135,237 S | 3/1943 | Bausch | D16/300 |
| D140,506 S | 3/1945 | Joyce | D16/300 |
| D141,029 S | 4/1945 | Splaine | D16/300 |
| D141,193 S | 5/1945 | Baratelli | D16/300 |
| D144,560 S | 4/1946 | Hansen | D16/300 |
| 2,537,047 A | 1/1951 | Gattern | 351/44 |
| D163,869 S | 7/1951 | Hinman | D16/300 |
| 2,630,569 A | 3/1953 | Baratelli et al. | 2/14 |
| D198,052 S | 4/1964 | Petitto | D16/300 |
| D198,996 S | 8/1964 | Lissac | D16/300 |
| D199,150 S | 9/1964 | Carmichael | D16/300 |
| D199,932 S | 12/1964 | Shindler | D16/300 |
| D199,933 S | 12/1964 | Shindler | D16/300 |

(List continued on next page.)

FOREIGN PATENT DOCUMENTS

| CA | 485155 | 7/1952 |
|---|---|---|
| FR | 1185637 | 8/1959 |
| FR | 1247974 | 2/1961 |

*Primary Examiner*—Huy Mai
(74) *Attorney, Agent, or Firm*—Cantor & Colburn LLP (57) ABSTRACT

Safety eyewear is presented which is provided with particulate sealing around the inside periphery of the lens/lenses and having temples that provide adjustment of the eyewear to a pantoscopic angle. The eyewear is provided with an adjustable strap assembly for better fit to the wearer's head. The eyewear lens/frame includes a plurality of projections that define various pantoscopic angles. The temple end piece includes a set of recesses that engage the projections formed on the lens/frame which temple end piece is rotated relative to the lens/frame to set the pantoscopic angle. The adjustable strap assembly further adjust the fit of the eyewear and can be unbuckled for snaplocked attachment of the eyewear directly to other safety equipment such as noise suppression ear muffs, communication head phones, breathing masks and the like.

10 Claims, 6 Drawing Sheets

U.S. PATENT DOCUMENTS

| | | | | |
|---|---|---|---|---|
| D201,393 S | 6/1965 | Thomas | | D16/300 |
| D202,129 S | 8/1965 | Marchi | | D16/300 |
| 3,218,765 A | 11/1965 | Volk | | 351/41 |
| D203,136 S | 12/1965 | Shindler | | D16/300 |
| 3,233,249 A | 2/1966 | Baratelli et al. | | 351/44 |
| 3,233,250 A | 2/1966 | Jonassen | | 351/44 |
| D204,957 S | 5/1966 | Dym | | D16/300 |
| 3,283,446 A | 11/1966 | Feinbloom | | 351/44 |
| 3,394,980 A | 7/1968 | Dym | | 351/41 |
| 3,526,449 A | 9/1970 | Boll″ et al. | | 351/44 |
| 3,544,204 A | 12/1970 | Bienenfeld | | 351/118 |
| 3,605,116 A | 9/1971 | Simpson et al. | | 351/41 |
| 3,623,800 A | 11/1971 | Volk | | 351/41 |
| 3,691,565 A | * 9/1972 | Galonek | | 2/452 |
| 3,708,224 A | 1/1973 | Lindblom | | 351/62 |
| 3,722,986 A | 3/1973 | Tagnon | | 351/44 |
| D228,028 S | 7/1973 | Leblanc et al. | | D16/300 |
| D228,583 S | 10/1973 | Leblanc | | D16/300 |
| D231,260 S | 4/1974 | Jelinek | | D16/300 |
| 3,907,410 A | 9/1975 | Richmond et al. | | 351/119 |
| 3,950,082 A | 4/1976 | Volk | | 351/41 |
| 4,002,439 A | 1/1977 | Volk | | 351/41 |
| 4,240,718 A | 12/1980 | Wichers | | 351/105 |
| D270,165 S | 8/1983 | Burns | | D16/44 |
| 4,564,272 A | 1/1986 | Kan | | 351/153 |
| 4,630,906 A | 12/1986 | Bammert et al. | | 351/159 |
| 4,670,915 A | 6/1987 | Evans | | 2/450 |
| 4,674,851 A | 6/1987 | Jannard | | 351/47 |
| 4,683,587 A | 7/1987 | Silverman | | 351/158 |
| 4,741,611 A | 5/1988 | Burns | | 351/44 |
| 4,786,125 A | 11/1988 | Magarinos et al. | | 350/3.65 |
| 4,810,080 A | 3/1989 | Grendol et al. | | 351/41 |
| 4,824,233 A | 4/1989 | Jannard | | 351/44 |
| 4,843,655 A | 7/1989 | Hegendörfer | | 351/44 |
| 4,859,048 A | 8/1989 | Jannard | | 351/47 |
| 4,867,550 A | 9/1989 | Jannard | | 351/47 |
| 4,955,087 A | 9/1990 | Pere″ et al. | | 351/41 |
| 4,955,706 A | 9/1990 | Schmidthaler et al. | | 351/41 |
| 4,977,627 A | 12/1990 | Metcalfe et al. | | 2/437 |
| 4,978,182 A | 12/1990 | Tedesco | | 350/3.7 |
| 5,032,017 A | 7/1991 | Boll″ et al. | | 351/44 |
| 5,050,981 A | 9/1991 | Roffman | | 351/177 |
| D323,333 S | 1/1992 | Jannard et al. | | D16/304 |
| 5,208,614 A | 5/1993 | Jannard | | 351/47 |
| 5,235,357 A | 8/1993 | Winthrop et al. | | 351/159 |
| 5,357,292 A | 10/1994 | Wiedner | | 351/105 |
| D354,067 S | 1/1995 | Lüzlbauer | | D16/300 |
| 5,379,463 A | 1/1995 | Schleger et al. | | 351/44 |
| 5,381,192 A | 1/1995 | Canavan et al. | | 351/118 |
| 5,387,949 A | 2/1995 | Tackles | | 351/44 |
| D358,828 S | 5/1995 | Jannard et al. | | D16/44 |
| 5,418,581 A | 5/1995 | Conway | | 351/116 |
| 5,426,473 A | 6/1995 | Riehm | | 351/44 |
| 5,457,505 A | 10/1995 | Canavan et al. | | 351/120 |
| 5,511,251 A | 4/1996 | Brakas | | 351/158 |
| 5,519,896 A | * 5/1996 | Ford | | 2/436 |
| 5,526,070 A | 6/1996 | Simioni | | 351/138 |
| 5,636,388 A | * 6/1997 | Hodges | | 2/443 |
| 5,659,381 A | 8/1997 | Simioni | | 351/120 |
| 5,706,360 A | * 1/1998 | Khandekar | | 351/156 |
| 5,748,281 A | * 5/1998 | Simioni et al. | | 351/121 |

* cited by examiner

PROTECTIVE EYEWEAR WITH ADJUSTABLE STRAP

CROSS-REFERENCE TO RELATED APPLICATIONS

This is a divisional of application Ser. No. 08/806,595 filed Feb. 26,1997 now U.S. Pat. No. 6,024,446 which is a continuation-in-part of application Ser. No. 08/641,901 filed May 2, 1996, now abadoned and application Ser. No. 08/770,920 filed Dec. 20, 1996, now U.S. Pat. No. 5,909, 267.

FIELD OF THE INVENTION

This invention relates generally to eyewear. More particularly, this invention relates both to plano (that is non corrective or zero power) and prescription eyewear for use in safety and recreational applications (i.e., sports and/or hostile environments) with adjustable strap temples which optionally permit the secure attachment of other safety equipment such as ear muffs or head phones.

BACKGROUND OF THE INVENTION

Protective eyewear, both prescription and plano (that is non corrective or zero power) is available in the market place for both safety and recreational (i.e., sports) applications. Such eyewear is exemplified in U.S. patent application Ser. No. 08/641,901 filed May 2, 1996, which is assigned to the assignee hereof, all of the contents of which are incorporated herein by reference. This eyewear comprises a pair of spectacles which includes a lens attached to a pair of temples. The lens has a surface which is created by rotating an aspheric shape about an axis which is offset from an axis of the aspheric shape. Preferably, the aspheric shape is an ellipse and more preferably the resultant lens will have a cross-section in the horizontal meridian which is a segment of an ellipse and a cross-section in the vertical meridian which is a segment of a circle. This lens exhibits a high degree of wrap and so provides extensive protection without the need for side shields.

Of course, many other prior art protective eyewear is known, all of the eyewear generally utilizing a pair of rigid or semi-rigid temples which extend outwardly from the lenses or a lens frame. Examples of other protective spectacles of this type include U.S. Pat. Nos. 4,867,550; 4,741, 611; 4,674,851; 4,859,048; 5,381,192 and 5,032,017, all of the contents of these patents being incorporated herein by reference.

One perceived problem not addressed by the prior art is that the prior art protective spectacles do not sufficiently protect the eyes from particulates that exist in dusty, dirty work environments. This dusty and dirty problem is also present for some sport environments. Currently, it is known that most common eye injuries in the industrial workplace are a result of these aforementioned particulates entering the area immediately adjacent to the eye. Therefore, there is a perceived need to develop eyewear that will keep particulate matter away from the eye. Additionally, in hostile environments, there is often a need to wear safety eyewear in conjunction with other safety equipment such as noise suppression ear muffs or communication head phones without disrupting the particulate seal of the eyewear or the seal of the other safety device or devices. Therefore, there is an additionally perceived need for a method of attachment of the eyewear to other safety gear without affecting the seals of the individual safety items as is presently unavoidable with prior art temples associated with prior art safety and protective spectacles.

SUMMARY OF THE INVENTION

The above-discussed and other problems and deficiencies of the prior art are overcome or alleviated by the novel protective eyewear with adjustable strap of the present invention. In accordance with the present invention, safety eyewear is provided with (1) a flange of resilient material (i.e., foam) for sealing about the periphery of the lenses of the eyewear (either prescription or plano) and (2) a novel temple and adjustable strap assembly so that the safety eyewear can be attached securely to a person's head and/or attached to other safety gear such as noise suppression ear muffs or head phones without breaking the seal of the eyewear or other safety equipment as can happen with conventional eyewear temples. The adjustable strap assembly in accordance with this invention assures an unbroken seal against particulates, noise leakage or signal loss. Additionally, the end piece of this temple provides pantoscopic angle adjustment for better fit.

The above-discussed and other features and advantages of the present invention will be appreciated and understood by those skilled in the art from the following detailed description and drawings.

BRIEF DESCRIPTION OF THE DRAWINGS

Referring to the Figures wherein like elements are numbered alike in the several Figures.

DESCRIPTION OF THE PREFERRED EMBODIMENT

Referring jointly to FIGS. 1–6, the protective eyewear with adjustable strap is shown generally at 10. Device 10 is comprised of three main sections including an eyewear lens 12 (shown generally in FIG. 5), a pair of strap holding temples 14 and 16 (best shown in FIGS. 1, 3, 4 and 6), and an adjustable strap assembly 18 (best shown also in FIGS. 1 and 6).

Lens 12 includes a resilient gasketing flange 22 which provides sealing around the periphery of the lens 20. Gasketing 22 is preferably a resilient foam. Lenses 12 are preferably the unitary, plano lenses depicted in FIGS. 13–15 of the aforementioned U.S. Ser. No. 08/641,901. However, it will be appreciated that lenses 12 may consist of any other suitable protective lenses (having an alternative shape) including but not limited to the lenses depicted in FIGS. 1–6 and 11–12 of U.S. Ser. No. 08/641,901 or the lenses in the aforementioned U.S. Pat. Nos. 4,867,550; 4,741,611; 4,674,851; 4,859,048; 5,381,192 and 5,032,017. Similarly, while in the preferred embodiment of the invention, no frames are provided for lenses 12, alternatively, the present invention may include a frame surrounding all or a portion of the lenses.

As discussed in detail in aforementioned U.S. Ser. No. 08/641,901, lens 12 is preferably a plano lens wherein the plano lens comprises a front surface curvature which is created by rotating an aspheric shape about an axis which is offset from an axis of the aspheric shape. In a preferred embodiment, the aspheric shape is an ellipse or at least is an aspheric shape, a segment of which has an elliptical arc. This elliptical arc is rotated about an axis spaced (offset) some distance from a major or minor axis of the ellipse. In a more preferred embodiment, the ellipse is rotated about an axis spaced from and parallel to the major or minor axis of the ellipse, but in the same plane as the ellipse. The resulting surface of this preferred lens configuration will have a cross-section in the horizontal meridian which is a segment of an ellipse, and a cross-section in the vertical meridian which is a segment of a circle. A significant feature of the preferred lens configuration is that the surface generated is rotationally symmetric. Additionally, while plastic lenses are preferred, eyewear made of safety glass or any other suitable material can be utilized in conformance with this invention.

Figure 1:
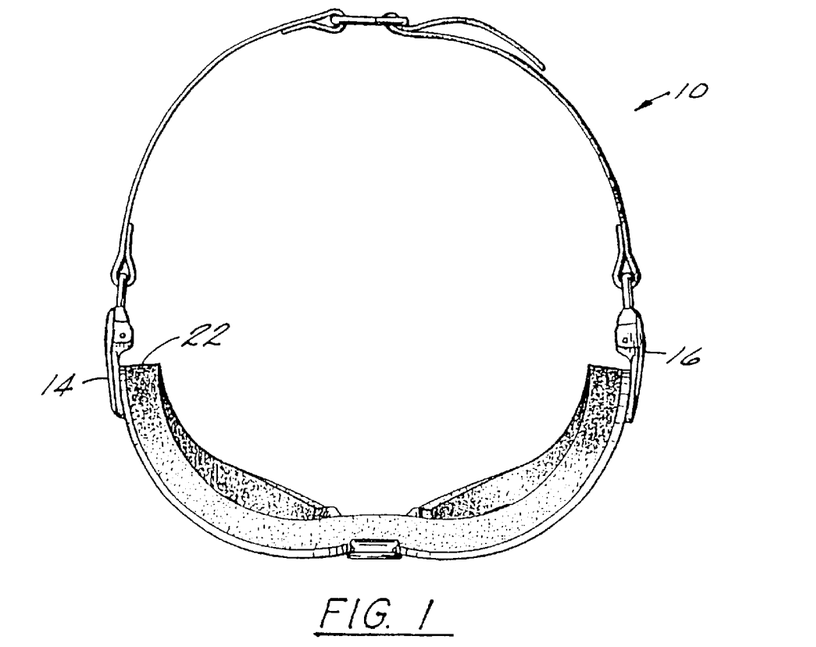
FIGS. 1–6 are respective top plan view, front elevation view, left side elevation view, right side elevation view, back elevation view and bottom plan views of the protective eyewear with adjustable strap in accordance with the present invention.
Figure 2:
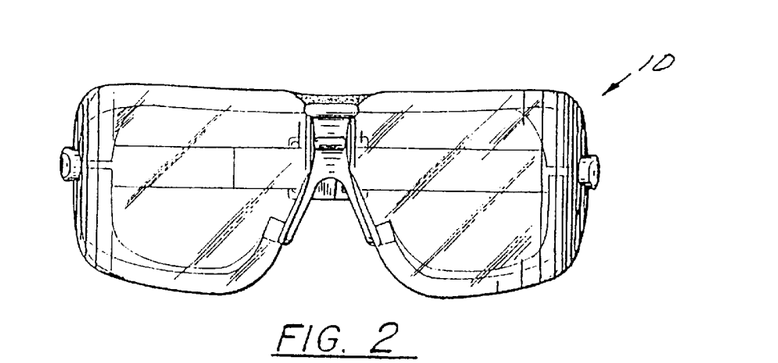
Figure 3:
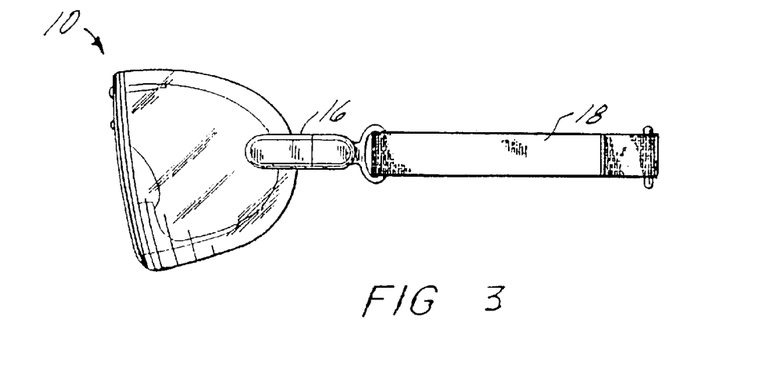
Figure 4:
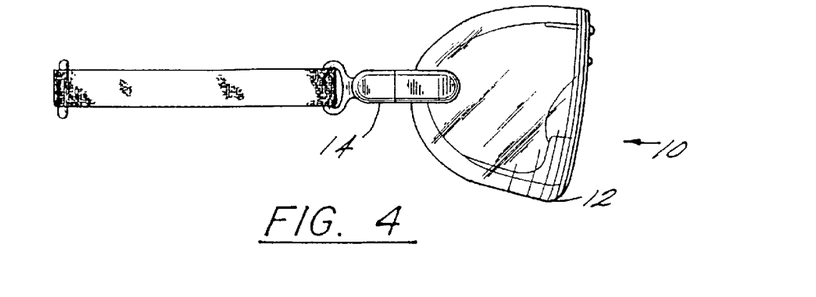
Figure 5:
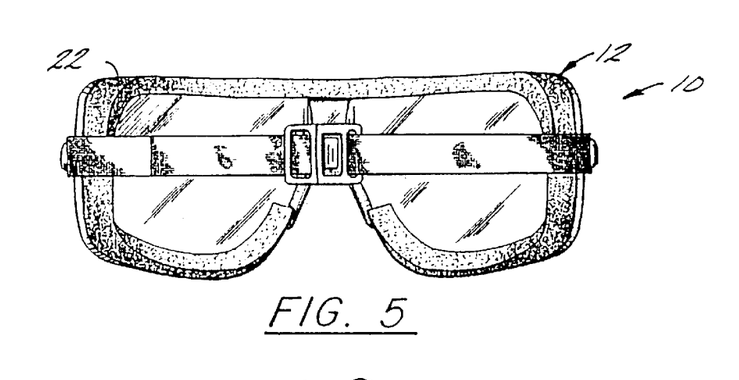
Figure 6:
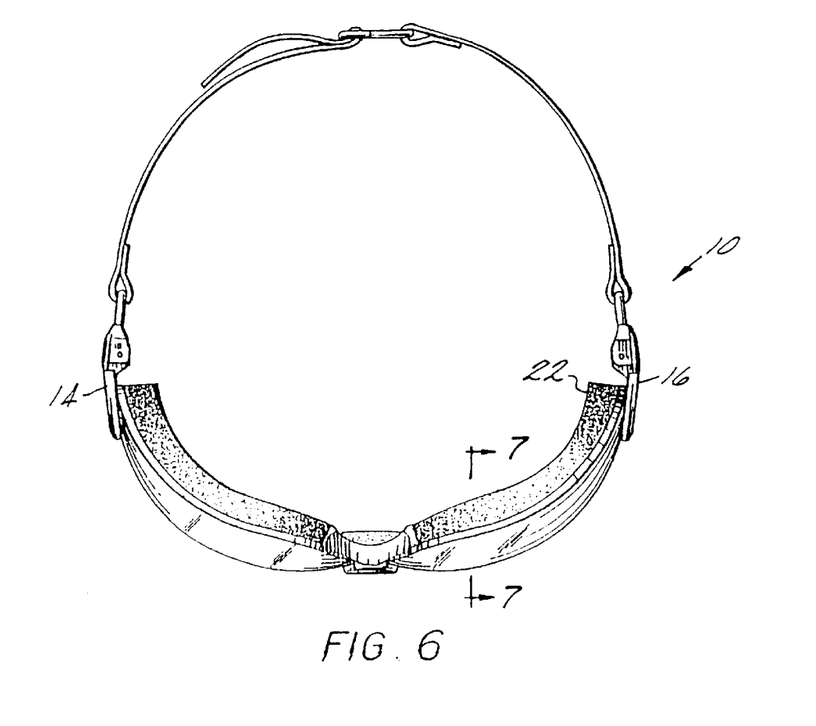
Figure 7:
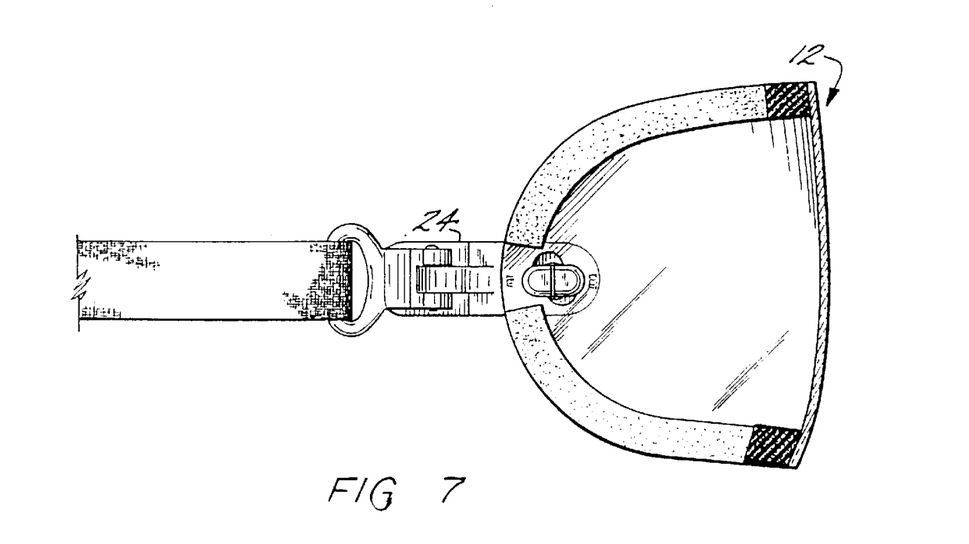
FIG. 7 is an enlarged side elevation cross-sectional view taken along the line 7—7 of FIG. 6.

Resilient flange 22 may be comprised of one or a plurality of strips which are adhesively applied along the periphery of lenses 12 or may be directly molded onto the lens. The flange 22 may be a single strip in which case it can be run along the entire periphery of the lens including those portions of the nosepiece and the hinge. Preferably, however, as shown in FIG. 7, the flange is broken at the hinges of the temples for ease of closing the temples during storage (the flange may also be broken at the nosepiece as shown in FIG. 5 since it may not be required in that area).

The foam flange 22 provides an important feature and advantage to the eyewear of the present invention. In particular, the foam flange 102 tends to minimize the probability of exposure of the wearer's eyes to particulates in a dusty, dirty work environment and/or in a similar dirty or dusty sports environment such as on a beach. Currently, the most common eye injury in the industrial workplace is the result of particulates in the eye. The use of the foam flange 22 will substantially reduce those incidences of eye damage caused by floating particulates for people who wear the eyewear of FIGS. 1–6. Of course as mentioned, the foam flange depicted in FIGS. 1–6 could also be used in connection with protective eyewear having a frame 25. Still another feature provided by the resilient flange of the present invention is that the flange, particularly by tailoring the softness and other characteristics of the foam, will improve the wearer's comfort, especially when the eyewear of this invention is worn for long periods of time.

Figure 8A:
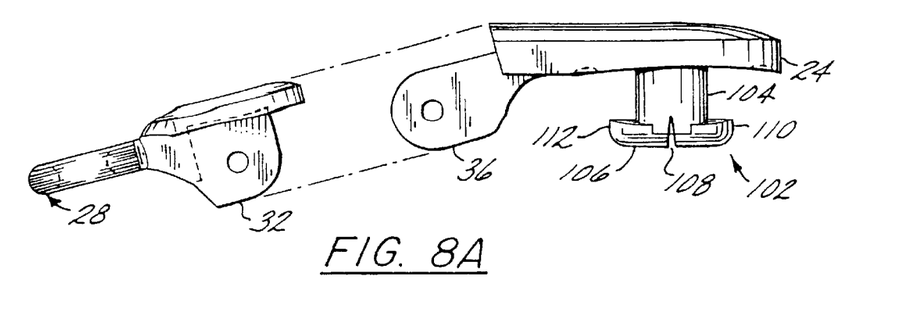
FIGS. 8A–8B are respective exploded enlarged top plan view and side elevation views of the strap holding temple prior to assembly of the protective eyewear with adjustable strap in accordance with the present invention of FIGS. 1–6.
Figure 8B:
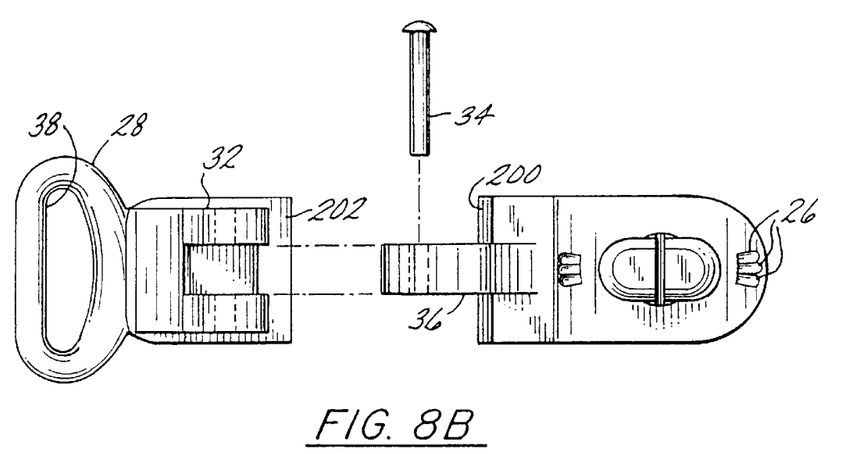

The eyewear of the present invention allows the user to hold the eyewear securely to the head by means of a unique adjustable strap or to use this adjustable strap to conveniently and securely attach the eyewear to another piece of safety equipment such as noise suppression ear muffs or communication head phones. FIGS. 8A–8B and FIG. 7 show the adjustable strap holding element 28. Strap holding element 28 includes a temple hinge 32. The temple hinge 32 is pivotally coupled to the end piece 24 (shown best in FIG. 7 and FIGS. 8A–8B) with a pin 34 (best seen in FIG. 8B) inserted through hinge element 36 to form a pivotable joint between end piece 24 and strap holding element 28. The pivotable joint between end piece 24 and strap element 28 allows the temples 14, 16 to fold one upon the other to enable the eyewear to take up minimum space when eyewear 10 is stored or not in use. This pivotal joint also acts to enhance the fit of the eyewear to the user's head by appropriately conforming the strap and eyewear as required. The material used for end piece 24 and strap holding element 28 is preferably a suitable moldable plastic. In a preferred embodiment, strap holding temples 14, 16 are connected directly to the upper, outer edges of the lens 12 (best seen in FIG. 7). Of course, as already mentioned it will be appreciated that lens 12 could just as well be connected to a frame instead of directly to a lens; in which case temples 14, 16 could be attached either to the lenses or to the frame.

The end piece 24 includes a post shown generally at 102 including a cylindrical neck 104 and a head 106. The end piece 24 includes recesses 26 that engage projections 52 formed on the exterior surface of the lens 12 (shown in FIG. 8D). A groove 108 is formed in the head 106 and a portion of the neck 104. The groove 108 has a v-shape where the width of the groove at one end is greater than the width of the groove at the other end. It is understood that alternative geometries may be used for groove 108. The groove 108 is formed generally perpendicular to the longitudinal axis of head 106 and extends across the entire head 106.

Figure 8C:
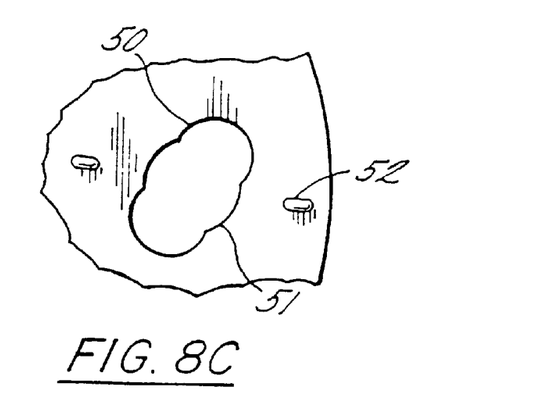
FIG. 8C is an enlarged view of a portion of the protective eyewear lens.

As shown in FIG. 8C, the lens 12 includes a slot 50 and projections 52 which cooperate with the end piece 24 to provide adjustment of the pantoscopic angle of the eyewear. Slot 50 is generally oval shaped and has a center circular area 51. Projections 52 are formed on the surface of the lens 12 and extend away from the lens surface. The recesses 26 engage projections 52 formed on lens 12. It is understood that projections may be formed on the end piece 24 and recesses formed in the lens 12.

The end piece 24 is coupled to the lens 12 by inserting the post 102 through slot 50 and rotating the end piece 24. To adjust the pantoscopic angle of the eyewear, the wearer rotates the end piece 24 and aligns one pair of the recesses 26 with the projections 52 formed on the lens 12. The groove 108 allows the distal ends 110 and 112 along the longitudinal axis of the head 106 to flex away from the lens 12. This allows the end piece 24 to rotate within the lens 12 more easily. This is particularly useful when the end piece 24 is first rotated upon insertion of the end piece into the lens 12 and when the pantoscopic angle is adjusted. The end piece 24 is made from a resilient material and the distal ends 110 and 112 of the head 106 apply pressure to the lens 13 and hold the end piece 24 at the desired pantoscopic angle.

The pantoscopic angle features of the present invention are preferably identical to the pantascopic angle features of commonly assigned U.S. patent application Ser. No. 08/770,920 filed Dec. 20, 1996 (all of the contents of which are incorporated herein by reference) except that the temple length adjustment housing 70 and temple tip 80 are replaced by the strap holding elements 28 and strap assembly 18 in the present invention. Therefore, reference is made to the application U.S. Ser. No. 08/770,920 for a additional details of the pantoscopic angle feature. The pantoscopic adjustment features assure for snug and comfortable fit especially when the protective eyewear of the present invention is combined with other safety devices.

Figure 9A:
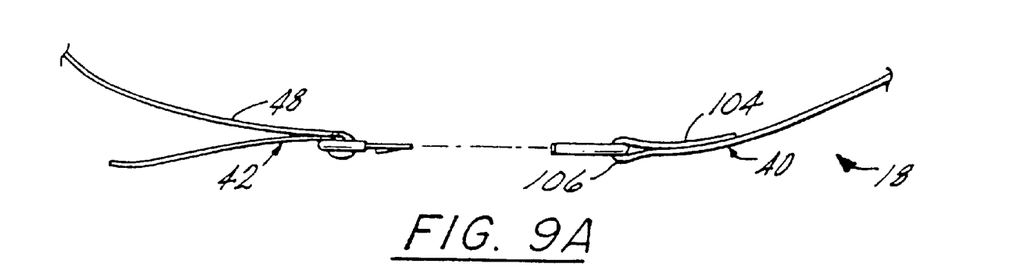
FIGS. 9A–9B are respective partial exploded top plan view and side elevation views of the connective buckle and strap portions of the adjustable strap in accordance with the present invention of FIGS. 1–6.
Figure 9B:
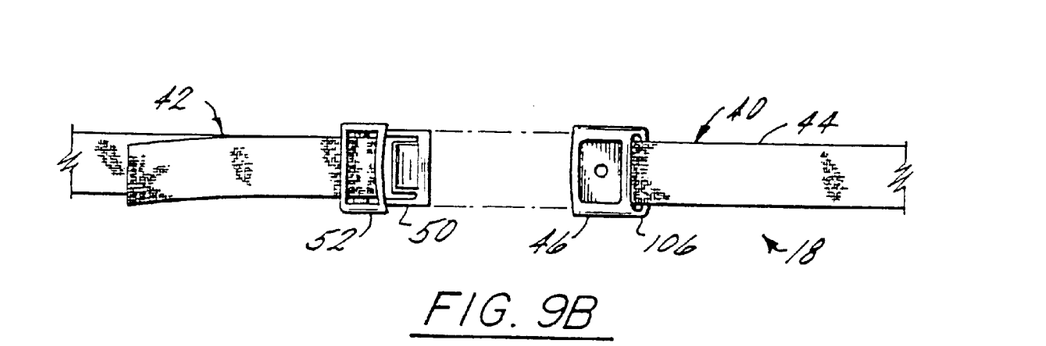

Strap holding element 28 has a smooth loop 38 sized to accept adjustable strap assembly 18. Adjustable strap assembly 18 (see FIGS. 9A–9B) is comprised of a right hand buckle and strap assembly generally shown at 40 and a left hand buckle and strap assembly generally shown at 42. Right hand buckle and strap assembly 40 is comprised of a suitable length of strap 44 and a snap-in female portion of buckle 46. Likewise, left hand buckle assembly 42 is comprised of a suitable length of strap 48, the male portion of snap-in buckle 50 which mates with the female portion of buckle 46 and a known strap tightening fastener 52 for adjusting the left hand strap 48 to the desired position for a secure mounting of the eyewear on a person's head to assure a snug and comfortable fit.

Strap portion 44 and strap portion 48 are suitably sized as is known in the industry and is preferably of known stretchable materials. Half buckle 46 and half buckle 50 and strap tightening fastener 52 are commercially available and should be of such material and finish as required by the environment where used. Both half buckle 46 and half buckle 50 have known snap connectors that snap into detents that exist on the outside of the safety ear muffs, head phones or any other safety device used in conjunction with the present invention eyewear.

It should be noted that strap 48 is longer than strap 44 because the extra length of strapping is needed to provide adequate adjustment of the adjustable strap assembly 18. It should be further noted that the end 104 of right hand strap 44 is folded over the loop 106 of buckle (half) 46 and extends a suitable distance and is assembled to a portion of strap 44 by known methods such as adhesives, welding or other known means.

Figure 10:
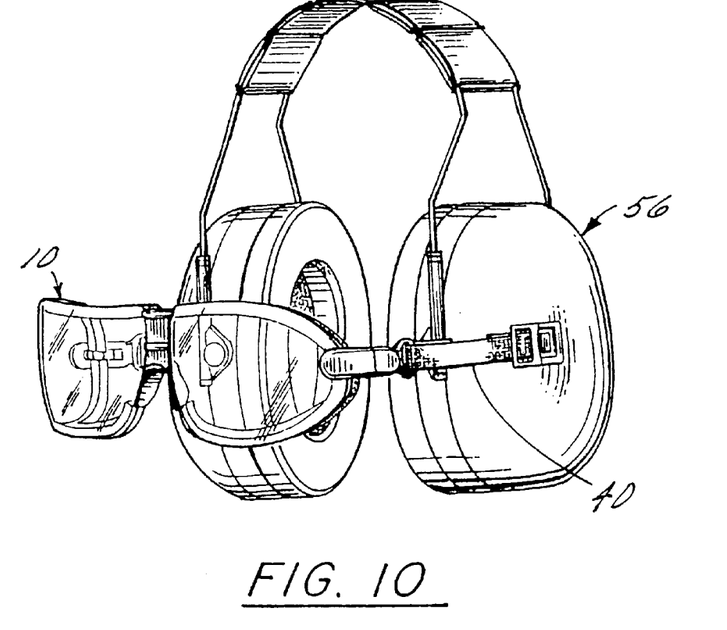
FIG. 10 is a perspective view of the protective eyewear with adjustable strap of FIGS. 1–6 combined with a set of protective ear muffs and/or head phones snap locked respectively to each ear muff and/or head phone.
Figure 11:
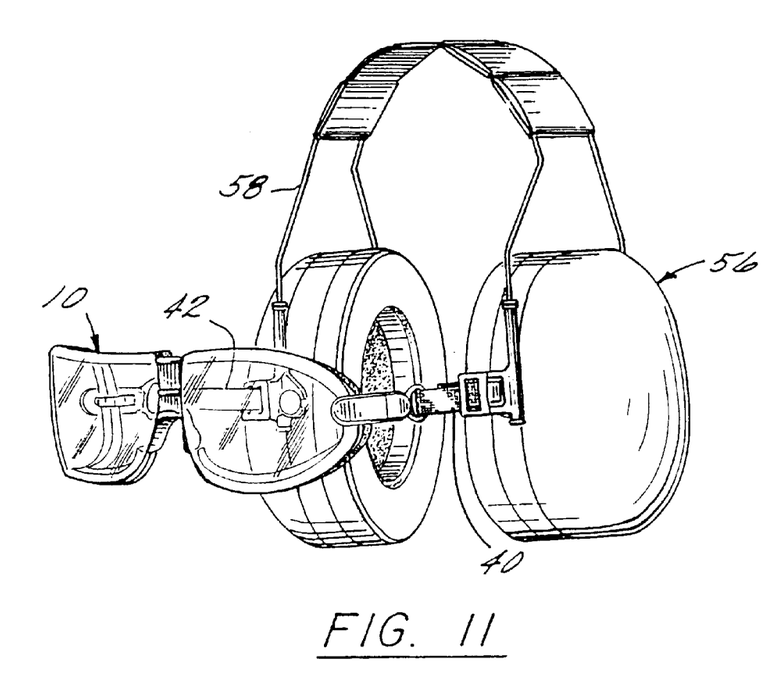
FIG. 11 is a perspective view of the protective eyewear with adjustable strap of FIGS. 1–6 combined with a set of protective ear muffs and/or head phones snap locked to the headband of the protective ear muffs and/or head phones.

FIG. 10 is a perspective view of the protective eyewear with adjustable strap 10 of FIGS. 1–6 in accordance with the present invention shown combined with a set of noise protective ear muffs and/or head phones generally shown at 56. Right hand buckle and strap assembly 40 has been unbuckled from left hand buckle and strap assembly 42. This allows right hand buckle and strap assembly 40 to be snap lockedly secured to the right ear muff of protective ear muff and/or head phones 56 and, likewise, left hand buckle and strap assemble 42 to be snap lockedly secured to the left ear muff of protective ear muff and/or head phones 56. Its can be seen that this arrangement provides for a secure and comfortable fit without breaking the seal of the protective ear muffs as would be the case with ordinary protective eyewear equipped with conventional temples. It should be further noted that other protective gear such as a breathing mask could be added to this arrangement with no problems. In an alternative embodiment shown in FIG. 11 the protective eyewear is snap lockedly secured to the headband 58 of the protective ear muff and/or head phones 56. It is understood that the protective eyewear 10 can be snap lockedly secured to any portion of the protective gear as long as the spatial relationship between the eyes and other portions of the wearer's head are maintained.

Figure 12:
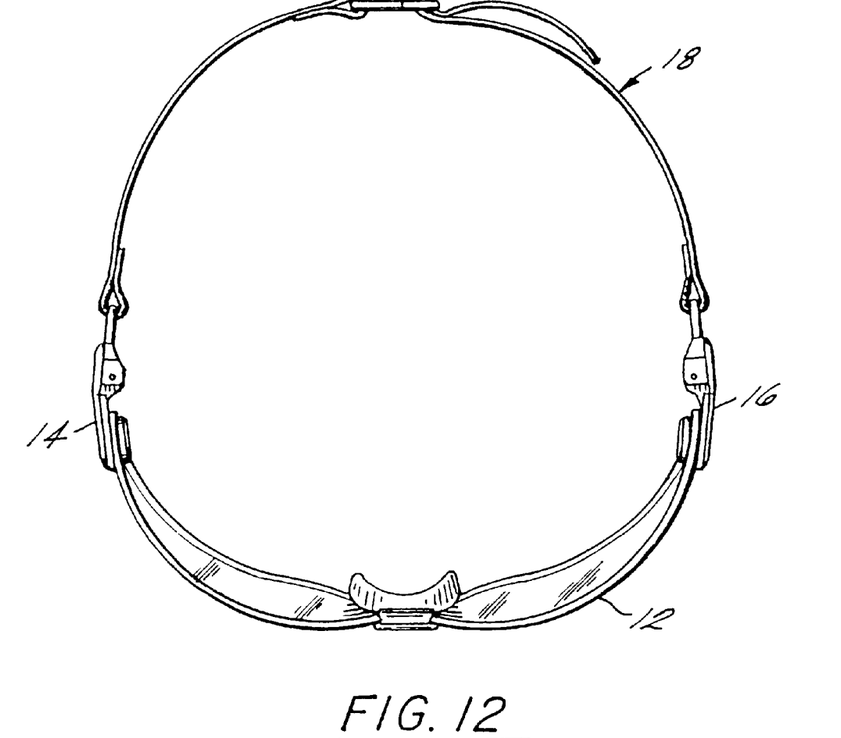
FIG. 12 is a top view of the protective eyewear in an alternative embodiment of the invention.
Figure 13:
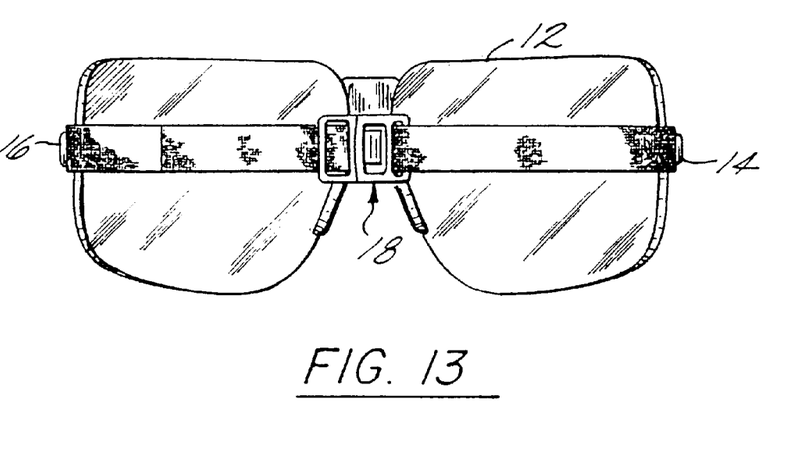
FIG. 13 is a rear view of the protective eyewear of FIG. 12.

FIG. 12 is a top view of the protective eyewear in an alternative embodiment of the invention. As shown in FIG. 12, the major portions of the protective eyewear are similar to those described above. In particular, the lens 12, temples 14, 16 and adjustable strap assembly 18 are the same as those described above with references to FIGS. 1–6. The gasketing 22, however, has been removed. FIG. 13 is a rear view of the protective eyewear of FIG. 12. The above described advantages of the temples 14 and 16 and the adjustable strap assembly 18 are still provided by the protective eyewear shown in FIGS. 12 and 13.

In accordance with a preferred embodiment of this invention, an anti-fog coating is applied to the inner surface of lenses 12 to enhance optical viewing. In the past, attempts to create such seal against particulate matter entry to the eye area have failed because of inability of the prior art to resolve the problem of fogging when the eyewear was worn for any length of time. Of course, any suitable anti-fog coating can be used in accordance with this invention; however a preferred anti-fog coating is commercially sold by Aearo Corporation of Southbridge, Mass. under the DX trademark.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. An ear and eye protective device comprising:
    hearing protector earmuffs including a pair of muff cups connected by a head band, at least one of said muff cups or said head band comprising a first fastener; and
    an eye protector removably connected to at least one of said muff cups or said head band, said eye protector including:
        a lens having opposed ends;
        a pair of end pieces, each of said end pieces including first and second end piece sections pivotably connected to one another and defining a hinge, each of said first end piece sections being attached to a respective end of said lens and each of said second end piece sections including an outer end which is opposed from an inner end, said inner end defining a portion of said hinge, each of said end piece sections comprising separate, elongated members such that each of said end pieces have a length extending outwardly of said respective ends of said lens and inwardly of the ear of a wearer when positioned about the head of a wearer; and
        a strap attached to each of said outer ends of said second end piece sections for retaining the lens in position about the head of a wearer wherein said strap is spaced from said hinge, said strap comprising a second fastener;
    wherein said first fastener is connectable with said second fastener such that said eye protector is removably connected with at least one of said muff cups or said head band.

2. The ear and eye protective device of claim 1, wherein said first fastener comprises a receiving member and said second fastener comprises a snap lock member, said snap lock member being inserted and releasably retained within said receiving member to provide said removable connection.

3. An ear and eye protective device comprising:
    hearing protector ear muffs including a pair of muff cups connected by a head band, at least one of said muff cups or said head band comprising a first fastener; and
    an eye protector removably connected to at least one of said muff cups or said head band, said eye protector including:

a lens having opposed ends;

a hinge connected to each of said opposed ends of said lens; and a strap attached to said hinge for retaining the lens in position about the head of a wearer said strap comprising a second fastener;

wherein said first fastener is connectable with said second fastener such that said eye protector is removably connected with at least one of said muff cups or said head band.

4. The ear and eye protective device of claim 3 wherein said first fastener comprises a receiving member and said second fastener comprises a snap lock member, said snap lock member being inserted and releasably retained within said receiving member to provide said removable connection.

5. A combined headphones and eye protective device comprising:

headphones including a pair of muff cups connected by a head band, at least one of said muff cups or said head band comprising a first fastener; and an eye protector removably connected to at least one of said muff cups or head band of said headphones, said eye protector including:

a lens having opposed ends;

a pair of end pieces, each of said end pieces including first and second end piece sections pivotably connected to one another and defining a hinge, each of said first end piece sections being attached to a respective end of said lens and each of said second end piece sections including an outer end which is opposed from an inner end, said inner end defining a portion of said hinge, each of said end pieces have a length extending outwardly of said respective ends of said lens and inwardly of the ear of a wearer when positioned about the head of a wearer; and a strap attached to each of said outer ends of said second end piece sections for retaining the lens in position about the head of a wearer wherein said strap spaced from said hinge, said strap comprising a second fastener;

wherein said first fastener is connectable with said second fastener such that said eye protector is removably connected with at least one of said muff cups or said head band.

6. The combined headphones and eye protective device of claim 5, wherein said first fastener comprises a receiving member and said second fastener comprises a snap lock member, said snap lock member being inserted and releasably retained within said receiving member to provide said removable connection.

7. An ear and eye protective device comprising:

hearing protector earmuffs including a pair of muff cups connected by a head band, at least one of said muff cups or said head band comprising a first fastener; and an eye protector removably connected to a least one of said muff cups or head band, said eye protector including;

a lens having opposed ends;

a hinge connected to each of said opposed ends of said lens; and a flexible strap attached to each of said hinges for retaining the lens in position about the head of a wearer, said strap comprising a second fastener;

wherein said first fastener is connectable with said second fastener such that said eye protector is removably connected with at least one of said muff cups or said head band.

8. The ear and eye protective device of claim 7, wherein said first fastener comprises a receiving member and said second fastener comprises a snap lock member, said snap lock member being inserted and releasably retained within said receiving member to provide said removable connection.

9. A combined headphones and eye protective device comprising:

headphones including a pair of muff cups connected by a head band, at least one of said muff cups or said head band comprising a first fastener; and an eye protector removably connected to at least one of said muff cups or head band, said eye protector including;

a lens having opposed ends;

a hinge connected to each of said opposed ends of said lens; and a flexible strap attached to each of said hinges for retaining the lens in position about the head of a wearer, said strap comprising a second fastener;

wherein said first fastener is connectable with said second fastener such that said eye protector is removably connected with at least one of said muff cups or said head band.

10. The combined headphones and eye protective device of claim 9, wherein said first fastener comprises a receiving member and said second fastener comprises a snap lock member, said snap lock member being inserted and releasably retained within said receiving member to provide said removable connection.

* * * * *